United States Patent [19]

Johnson et al.

[11] Patent Number: 4,578,517

[45] Date of Patent: Mar. 25, 1986

[54] POLYALKYLENE POLYAMINES FROM ALKANOLAMINE AND AMMONIA OR AMINES USING GROUP IIIB METAL ACID PHOSPHATE CATALYSTS

[75] Inventors: Thomas A. Johnson, Orefield; Michael E. Ford, Center Valley, both of Pa.

[73] Assignee: Air Products and Chemicals, Inc., Allentown, Pa.

[21] Appl. No.: 533,319

[22] Filed: Sep. 16, 1983

[51] Int. Cl.[4] ............................................. C07C 85/06
[52] U.S. Cl. ................... 564/479; 564/511; 564/512; 544/358; 544/402; 260/239 BC
[58] Field of Search ............ 564/479, 478, 469, 503, 564/511, 512; 544/358, 402; 260/239 BC

[56] References Cited

U.S. PATENT DOCUMENTS

| | | | |
|---|---|---|---|
| 3,270,059 | 8/1966 | Winderl et al. | 564/469 |
| 3,520,933 | 7/1970 | Adam et al. | 564/374 |
| 3,714,259 | 1/1973 | Lichtenwalter et al. | 564/480 |
| 3,755,447 | 8/1973 | Klemann et al. | 564/461 |
| 3,766,184 | 10/1973 | Johansson et al. | 544/358 |
| 4,014,933 | 3/1977 | Boettger et al. | 564/447 |
| 4,036,881 | 7/1977 | Brennan et al. | 564/479 |
| 4,044,053 | 8/1977 | Brennan et al. | 564/479 |
| 4,316,840 | 2/1982 | Ford et al. | 260/239 BC |
| 4,316,841 | 2/1982 | Ford et al. | 260/239 BC |
| 4,324,917 | 4/1982 | McConnell | 564/479 |
| 4,405,784 | 9/1983 | Wells | 544/352 |
| 4,446,320 | 5/1984 | Eskinazi et al. | 544/100 |

*Primary Examiner*—Charles F. Warren
*Attorney, Agent, or Firm*—Michael Leach; James C. Simmons; E. Eugene Innis

[57] ABSTRACT

A process for preparing polyalkylene polyamine compounds is disclosed wherein ammonia or a primary or secondary amine and an alkanolamine compound are reacted in the presence of an effective amount of a Group IIIB metal acid phosphate at a temperature from about 175° to 400° C. under a pressure sufficient to maintain a substantial amount of the ammonia or amine in the reaction zone. The polyalkylene polyamines thus formed are recovered from the reaction mixture.

42 Claims, No Drawings

POLYALKYLENE POLYAMINES FROM ALKANOLAMINE AND AMMONIA OR AMINES USING GROUP IIIB METAL ACID PHOSPHATE CATALYSTS

TECHNICAL FIELD

This invention relates to the preparation of polyalkylene polyamines, particularly the preparation of such polyamines using a phosphorus containing catalyst.

BACKGROUND OF THE INVENTION

Low molecular weight polyethylene polyamines are used in a wide variety of applications such as corrosion inhibitors, fabric softeners, lubricating oil additives, fungicides and many others. Despite the utility of polyethylene polyamines, they are currently obtained only as by-products of ethylenediamine manufactured by the reaction of ethylene dichloride with excess ammonia. Since the polyamines are by-products of ethylenediamine preparation, the supply and quality of available polyethylene polyamines are often variable. Moreover, since sodium chloride is co-produced in large quantities, separation of the products from the sodium chloride and the handling and disposal of this corrosive inorganic salt require special measures.

The prior art discloses various attempts to circumvent these difficulties and to provide controllable, efficient routes to polyethylene polyamines:

U.S. Pat. No. 4,036,881 discloses the preparation of polyalkylene polyamines by reacting an alkanolamine with an alkyleneamine compound in the presence of a phosphorus containing substance selected from the group consisting of acidic metal phosphates, phosphoric acid compounds and anhydrides and the phosphate esters.

U.S. Pat. No. 4,044,053 is somewhat similar to the '881 patent except that the alkyleneamine compound is present in an excess amount and a diol is used in place of the alkanolamine.

U.S. Pat. No. 4,324,917 discloses ion exchange resins containing phosphonic acid functionality as catalysts for production of polyethylene polyamines by alkylation of alkyleneamines such as ethylenediamine with alkanolamines such as monoethanolamine.

U.S. Pat. No. 4,314,083 discloses a process for selectively preparing predominantly noncyclic polyalkylene polyamines by reacting an alkanolamine with an alkyleneamine compound in the presence of a salt of a nitrogen or sulfur containing substance or the corresponding acid.

U.S. Pat. No. 3,714,259 discloses the preparation of linear polyethylene amines by contacting ethanolamine with ethylenediamine compound in the presence of hydrogen and a hydrogenation catalyst. An example of a hydrogenation catalyst is nickel containing copper and chromium components. Significant amounts of water are included in the feedstock, mainly 25 to 50 wt % based on the combined starting ethylenediamine and monoethanolamine.

U.S. Pat. No. 3,766,184 discloses the reductive amination of monoethanolamine by metallic catalysts of iron and nickel and/or cobalt in the presence of hydrogen.

The prior art requires a source of preformed ethylenediamine for reaction with monoethanolamine to produce polyethylene amines. The production of ethylenediamine is an additional process step which extends and complicates the prior art routes to polyethylene amines. Thus, production of polyethylene amines requires preparation of substantial quantities of both monoethanolamine, the alkylating agent, and ethylenediamine, the aminating agent, in separate steps and subsequent copolymerization of the monomers to provide polyethylene amines. Prior art routes to polyethylene polyamines are therefore limited by their dependency on a sufficient supply of preformed ethylenediamine in the reactions.

SUMMARY OF THE INVENTION

It has been found that polyalkylene polyamines are produced in good yield directly by reacting ammonia or a primary or secondary amine with an alkanolamine compound in the presence of a catalytically effective amount of a Group IIIB metal acid phosphate at a temperature sufficient to effect reaction between the ammonia or amine and the alkanolamine under a pressure sufficient to maintain the a substantial amount of the ammonia or amine in the reaction zone.

As an advantage of the invention the reaction of monoalkanolamine with ammonia or a primary or secondary amine provides polyalkylene polyamines directly as the major reaction products. The process does not require an alkylenediamine as a feedstock for making the polyalkylene polyamines. Moreover, a wide range of polyamine products is provided.

As a further advantage the use of Group IIIB metal acid phosphates as catalysts avoids problems associated with co-production of stoichiometric quantities of an inorganic salt.

Furthermore, in contrast to many Group IA acid phosphates, Group IIIB metal acid phosphates are insoluble in the reaction medium. Thus, under conditions for operation of this process, Group IIIB metal acid phosphates are insoluble solids that are easily localized in a fixed bed or continuous stirred tank reactor. Isolation of polyamine products, particularly in continuous processes, is, therefore, readily accomplished.

DETAILED DESCRIPTION OF THE INVENTION

The invention relates to a process for synthesizing cyclic and noncyclic polyalkylene polyamines, preferably linear polyethylene polyamines such as diethylenetriamine and higher homologs. In the process ammonia or a primary or secondary amine is reacted with an alkanolamine having a primary or secondary hydroxy moiety and an amino group. Preferably, the alkanolamine has an unbranched alkylene moiety.

The alkanolamine compounds which are used in practicing the process include those represented by the general formula:

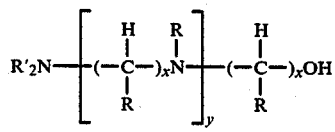

where R is hydrogen or a lower alkyl ($C_1$-$C_4$) radical, R', is hydrogen or an alkyl ($C_1$-$C_{24}$) radical, x is a number from 2 to about 6, and y is a number from 0 to 3. Exemplary of suitable alkyl radicals are the lower ($C_1$-$C_4$) alkyls, such as methyl, ethyl and butyl, and higher alkyls such as octyl, decyl and octadecyl. Methyl is the preferred lower alkyl radical. However, it is preferred that R and R' be hydrogen. Thus, the alkanolamine would contain a primary amino group. Examples of alkanolamine compounds that can be used are the ethanolamines, isomeric propanolamines, N-(2-aminoethyl)ethanolamine, N-methylethanolamine, N,N-dimethylethanolamine, N,N,N'-trimethylaminoethylethanolamine and the like.

Ammonia and the primary and secondary amines which can be used in the process can be represented by the general formula

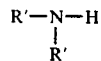

where R' is hydrogen or an alkyl ($C_1$-$C_{24}$) radical, preferably a lower alkyl ($C_1$-$C_4$) radical, such as methyl or ethyl. Proposed amine feedstocks include monomethylamine, dimethylamine, monoethylamine, diethylamine, octylamine and octadecylamine.

Noncyclic polyalkylene polyamines that are produced by the reaction of ammonia and an alkanolamine are represented by the general formula:

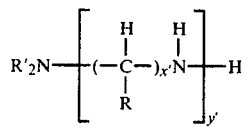

where R is hydrogen or a lower alkyl ($C_1$-$C_4$) radical, R' is hydrogen or an alkyl ($C_1$-$C_{24}$) radical, preferably a methyl radical, x' is a number from 2 to about 6, y' is a number from 2 to about 7, and x' may vary for a given value of y'. Examples of noncyclic polyalkylene polyamines that are produced include dipropylenetriamine, tributylenetetramine, di(2-methylethylene)triamine, tri(2-methylethylene)tetramine, N-(2-aminoethyl)-1,3-propylenediamine, diethylenetriamine, and the noncyclic isomers of triethylenetetramine and tetraethylenepentamine.

Use of secondary amines instead of ammonia would lead to polyamines containing terminal dialkylamino groups. Alternatively, use of primary amines instead of ammonia would lead to polyamines which contain randomly distributed monoalkylamino groups.

Particularly when monoethanolamine is reacted with ammonia, cyclic polyethylene polyamines are obtained as products. Examples of such cyclic polyethylene polyamines that are produced include piperazine, N-(2-aminoethyl) piperazine, and cyclic isomers of triethylenetetramine, tetraethylenepentamine, and pentaethylenehexamine.

One embodiment of the invention comprises a continuous process for preparing polyalkylene polyamines by (a) adding a charge consisting essentially of ammonia or a primary or secondary amine and an alkanolamine compound to a reaction zone containing a catalytically effective amount of a Group IIIB metal acid phosphate at a temperature sufficient to effect a reaction between the ammonia or amine and the alkanolamine compound under a pressure sufficient to maintain a substantial amount of the ammonia or amine in the reaction zone to produce a reaction product stream containing ammonia or primary or secondary amine, alkanolamine compound, and polyalkylene polyamines, and (b) withdrawing the product stream from the reaction zone and separating it to provide a polyalkylene polyamine stream and ammonia or the primary or secondary amine and alkanolamine compound which are recycled to the reaction zone.

The invention can also be viewed as a method for avoiding the inclusion of alkyleneamine compound in the feed to the reaction zone in a continuous process for the preparation of polyalkylene polyamines which continuous process comprises continuously adding a feed containing an alkanolamine compound to a reaction zone containing a catalyst to yield a product stream comprising the polyamines and alkanolamine compound, separating the desired polyamines from the product stream and recycling the alkanolamine compound to the reaction zone. The method of the invention would comprise (a) adding ammonia or a primary or secondary alkylamine to the feed to the reaction zone, (b) using a catalytically effective amount of a Group IIIB metal acid phosphate as the catalyst, and (c) effecting the reaction under a pressure sufficient to maintain a substantial amount of the ammonia or amine in the reaction zone.

The catalysts which are suited for practicing the process of the invention are Group IIIB metal acid phosphates including Group IIIB metal phosphates, monohydrogen phosphates, dihydrogen phosphates and mixtures thereof. While the intent of the catalyst preparations described hereinafter was to specifically provide a particular Group IIIB monohydrogen phosphate or dihydrogen phosphate, mixtures of the Group IIIB metal phosphates of the above-mentioned types may be obtained owing to complicated dependence of the catalyst composition on preparation conditions. Nevertheless, although the Group IIIB metal acid phosphate catalyst of the invention comprises the metal phosphate, monohydrogen phosphate, dihydrogen phosphate or mixtures thereof, the monohydrogen and dihydrogen phosphate of the Group IIIB metals would be the preferred catalysts if obtainable in relatively pure form individually or in combination.

A Group IIIB metal is meant to include scandium, yttrium, lanthanum and the rare earth lanthanide metals having atomic numbers 58-71, and the rare earth actinides having atomic numbers 89 to 92.

The preferred catalysts for the production of polyalkylene polyamines include the acid phosphates, preferably the monohydrogen phosphates and dihydrogen phosphates, of scandium, lanthanum, cerium, samarium, europium, thulium, erbium, ytterbium, yttrium, lutetium, thorium, neodymium, praseodymium, dysprosium and gadolinium.

The acid phosphate catalysts may be used for the production of polyamines either singly or in combination. As might be expected, it is preferred to use those which are more catalytically active and provide for substantial conversion to the polyalkylene polyamine products. The preferred catalyst compounds include lanthanum monohydrogen phosphate, lanthanum dihydrogen phosphate, lanthanum phosphate, praseodymium monohydrogen phosphate, praseodymium dihydrogen phosphate, praseodymium phosphate, neodymium monohydrogen phosphate, neodymium dihydrogen phosphate, neodymium phosphate and mixtures thereof.

The quantity of the acid phosphate salts of Group IIIB metals used in the reaction can vary widely depending upon the reactivity of the catalysts and the reactivity of the reactants present. A catalytically effective amount of material is used; in other words, an amount which causes a reaction between the ammonia or amine and the alkanolamine to yield polyalkylene polyamine products at the temperature and pressure used. Usually, though, the amount used to provide a catalytic effect ranges from about 0.1 to 25 weight % based upon alkanolamine present in the reaction mixture, and preferably about 0.1 to 20 weight %. Within these ranges though, the level of catalyst is empirical and is adjusted depending on the product slate desired.

In the preparation of polyalkylene polyamines the reaction is maintained at a temperature from about 175° C. to about 400° C., and preferably is carried out between 210° C. and 350° C. to obtain a practical rate of polyamine production without generation of excessive levels of high molecular weight products.

The pressure utilized for carrying out the reaction is that pressure which is sufficient to maintain a substantial amount of the ammonia or amine in the reaction zone and may, for example, range from 10 to 350 atm in batch reactions, but preferably is that autogenous pressure which is sufficient to maintain the reaction substantially in liquid phase, although higher pressures can be used.

By reaction zone is meant that vessel, e.g., autoclave, continuous stirred tank reactor or packed bed reactor, in which the catalyst is localized and production of polyamines is effected.

Although the reactions can be carried out in the batch mode, they are also amenable to continuous processes, for example operation of a continuous stirred tank reactor or a packed bed reactor. The reaction is allowed to proceed until a desired conversion is obtained or the reaction is complete. Normally the reaction is carried out within about 0.5 to 5 hours in the batch mode or residence times (based on alkanolamine) of 0.01 to 4.0 hours in a continuous mode for practical levels of polyamine production. For continuous reactions, such as those carried out at controlled pressures in a fixed bed reactor or in a continuous stirred tank reactor, the pressure utilized for the reaction may range from 1 to 150 atm. Reaction pressure must be sufficiently high, preferably at least 75 psig, to maintain a significant portion of the ammonia or lower alkyl amine in the reaction zone. Preferred reaction times and catalyst levels depend on catalyst reactivity and are adjusted empirically. Thus, for example, relatively lower catalyst incorporations and shorter reaction times are preferred for the production of polyamines with more reactive catalysts.

Generally, the mole ratio of ammonia or amine to alkanolamine compound may range from about 1:1 to 10:1, and preferably is about 2:1 to 5:1. It is advantageous in carrying out the process that the proportion of ammonia to alkanolamine, especially monoethanolamine, compound be in stoichiometric excess, e.g., from about 2:1 up to 5:1, to control product formation so that primarily dimeric to pentameric polyethylene amines are formed without the necessity of handling excessively large recycle streams.

Recovery of the polyalkylene polyamines from the reaction mixture can be accomplished by conventional techniques, these techniques generally involving a distillation. Often a small amount of a salt, such as the one used as the catalytic material, is added to the polyalkylene polyamine separation purification as described in U.S. Pat. No. 3,755,447.

The catalysts used in the process of the invention can be prepared by the precipitation of the desired metal acid phosphate salt, washing to remove inorganic co-products, and drying. Optionally, dried catalysts may be further processed prior to use for polyamine manufacture. Such processing is well known to those skilled in the art and may include extrusion or pelletizing, or compounding with an inert support such as alpha-alumina. Preparation of two lanthanum acid phosphates are illustrative of the general procedure by which these catalysts are made.

PREPARATION OF LANTHANUM ACID PHOSPHATE CATALYSTS

CATALYST A

Lanthanum nitrate hexahydrate (130 g, 0.30 mole) was dissolved in deionized water (150 ml) with stirring. Diammonium hydrogen phosphate (79.2 g, 0.60 mole) was dissolved in deionized water (140 ml) with stirring. While a solution of diammonium hydrogen phosphate was vigorously stirred, the solution of lanthanum nitrate was added in one portion over a period of 5 to 10 seconds. A thick, lumpy precipitate formed immediately. After 10 minutes of manual stirring, a thick, creamy suspension resulted. Vacuum filtration to isolate the precipitate was started within one-half hour of the time of addition of the solutions. Complete separation of the filtrate required 5 to 6 hours, owing to the very finely divided nature of the precipitate. The resulting pasty solid was washed sequentially with three 100 ml portions of deionized water. After washing, the filter cake was dried at 80–90° C. to constant weight to afford 113 g of a lanthanum acid phosphate (Catalyst A).

CATALYST B

The above procedure was repeated using the following solutions to obtain 60 g of a second lanthanum acid phosphate (Catalyst B):

Ammonium dihydrogen phosphate—86.25 g (0.75 mole) in 300 ml deionized water.

Lanthanum nitrate hexahydrate—108.25 g (0.25 mole) in 150 ml deionized water.

In those cases where the preparation of the Group IIIB metal acid phosphate results in a gel-like product isolation of the catalyst by filtration may be facilitated by the addition of 10 to 15% of a diatomaceous silica filter aid to the ammonium phosphate solution to form a slurry prior to adding the Group IIIB metal nitrate solution.

With regard to the preparation of a lanthanum acid phosphate catalyst, it is preferred that the lanthanum nitrate solution be prepared by diluting with water commercially available concentrated lanthanum nitrate solution having a pH of about 2 to 3. The diluted solution is then added to an aqueous ammonium phosphate solution which had been previously adjusted to a pH of about 7 with ammonium hydroxide. The final pH of the mixture should be about 6.5 where the molar ratio of the lanthanum to phosphate is about 1:3.

See also U.S. Pat. No. 3,752,878 for the preparation of rare earth metal phosphates.

The intent of the above-described lanthanum acid phosphate catalyst preparations is to provide a general procedure to prepare the desired Group IIIB metal monohydrogen phosphate or dihydrogen phosphate. However, phosphate-containing materials may be obtained which consist predominantly of the Group IIIB metal phosphate, the Group IIIB metal monohydrogen phosphate, the Group IIIB metal dihydrogen phosphate, or mixtures in varying proportions of the Group IIIB metal mono- and dihydrogen phosphate, and/or mixtures in varying proportions of any of the above Group IIIB metal acid phosphates with the Group IIIB metal phosphate. Such variations in catalyst composition may result from complicated dependence of the catalyst composition on preparation conditions, such as temperature, concentration of reagents, stoichiometry of reagents, rate and order of reagent addition, pH of preparation, duration of preparation, volume and pH of waterwash, duration of catalyst washing, and duration and temperature of catalyst drying. In any event, the Group IIIB metal acid phosphates obtained according to the general preparations described above for lanthanum acid phosphates are catalytically active as exemplified for the production of polyamines in the following examples.

The following examples which illustrate the nature of the process are not intended to limit the scope of the invention. In each example the reactions were carried out under the indicated conditions either in a stirred 300 ml autoclave under that autogenous pressure which was sufficient to maintain a significant portion of the reaction in liquid phase or in a fixed bed packed reactor. Such pressures ranged from 1400 to 4200 psig, depending on the feed ratio, in the autoclave. In a fixed bed packed reactor the back pressure regulator was set at 300 psig.

For purposes of brevity the products obtained are often abbreviated in the following Tables. The compound abbreviations are:

EDA—ethylenediamine
PIP—piperazine
AEP—aminoethylpiperazine
DETA—diethylenetriamine
TETA(NC)—triethylenetetramine (noncyclic isomers)
TETA(C)—triethylenetetramine (cyclic isomers)
TEPA(NC)—tetraethylenepentamine (noncyclic isomers)
TEPA(C)—tetraethylenepentamine (cyclic isomers)
HVY(NC)—pentaethylenehexamine and higher oligomeric polyethylene amines (noncyclic isomers)
HVY(C)—pentaethylenehexamine and higher oligomeric polyethylene amines (cyclic isomers)
AEEA—aminoethylethanolamine

EXAMPLE 1

A mixture of monoethanolamine (63.3 g, 1.04 mole), ammonia (35.5 g, 2.09 mole), and lanthanum acid phosphate Catalyst A (12.2 g) was placed in a 300 ml stainless steel stirred autoclave. The mole ratio of ammonia:monoethanolamine was 2:1; catalyst incorporation was 19.3 wt. % based on monoethanolamine. The mixture was heated to 300° C. for 2.0 hours during which time autogenous pressure of 1900 psig developed. During the reaction, the mixture was stirred at 2,000 rpm. Analysis of the cooled reaction mixture by gas-liquid chromatography indicated substantial conversion of monoethanolamine to a mixture of polyamines. Tables 1 and 2 provide additional experimental details and product analysis.

EXAMPLES 2-8

The above procedure was repeated with a series of Group IIIB metal acid phosphate-A catalysts. Catalysts designated as "metal acid phosphate-A" were prepared from the corresponding metal nitrate and diammonium hydrogen phosphate by the procedure exemplified above for lanthanium acid phosphate Catalyst A. Additional experimental details and product analysis are shown in Tables 1 and 2.

TABLE 1

| Example | Catalyst | Catalyst Level (wt. %)[a] | Temp (°C.) | Time (hr) | Mole Ratio (MEA/NH3)[b] | Conversion (%)[d][c] | Selectivity (NC)[e] | Selectivity (AEEA)[f] |
|---|---|---|---|---|---|---|---|---|
| 1 | Lanthanum Acid Phosphate-A | 19.3 | 300 | 2 | 1/2 | 53 | 54 | 8 |
| 2 | Lanthanum Acid Phosphate-A | 18.5 | 300 | 4 | 1/4 | 50 | 63 | 26 |
| 3 | Neodymium Acid Phosphate-A | 19.3 | 300 | 2 | 1/2 | 68 | 38 | 10 |
| 4 | Yttrium Acid Phosphate-A | 15.7 | 300 | 1 | 1/2 | 63 | 32 | 31 |
| 5 | Yttrium Acid Phosphate-A | 7.8 | 300 | 2 | 1/2 | 54 | 27 | 34 |
| 6 | Yttrium Acid Phosphate-A | 15.7 | 300 | 2 | 1/2 | 67 | 40 | 13 |
| 7 | Gadolinium Acid Phosphate-A | 20.3 | 300 | 2 | 1/2 | 70 | 35 | 6 |
| 8 | Praseodymium Acid Phosphate-A | 19.2 | 300 | 2 | 1/2 | 80 | 43 | 4 |

[a]Based on monoethanolamine (MEA).
[b]Mole ratio of monoethanolamine:ammonia in the feedstock.
[c]Results are derived from analyses presented in Table 2, and are rounded off to the the nearest integer.
[d]Based on unchanged monoethanolamine.
[e]Weight percent of linear and branched polyethylene amines in total polyamine product.
[f]Weight percent of aminoethylethanolamine (AEEA) in total polyamine product.

TABLE 2[a]

| Example | EDA | PIP | AEP | DETA | TETA(NC) | TETA(C) | TEPA(NC) | TEPA(C) | HVY(NC) | HVY(C) | AEEA |
|---|---|---|---|---|---|---|---|---|---|---|---|
| 1 | 34.79 | 6.96 | 13.75 | 9.10 | 3.93 | 10.54 | 5.13 | 6.30 | 1.17 | 0.81 | 7.50 |
| 2 | 49.23 | 4.94 | 3.84 | 10.17 | 1.70 | 1.70 | 1.90 | 0.00 | 0.00 | 0.00 | 26.46 |
| 3 | 12.33 | 9.94 | 12.27 | 11.52 | 3.19 | 10.74 | 4.18 | 11.55 | 6.65 | 10.83 | 9.81 |
| 4 | 17.26 | 8.01 | 8.41 | 8.11 | 1.92 | 9.64 | 2.26 | 8.46 | 2.11 | 2.95 | 30.88 |
| 5 | 16.09 | 7.02 | 8.73 | 4.78 | 2.54 | 10.34 | 3.12 | 9.22 | 1.12 | 2.68 | 34.37 |
| 6 | 14.78 | 6.91 | 11.78 | 12.40 | 3.10 | 12.07 | 3.71 | 9.91 | 5.97 | 6.62 | 12.75 |
| 7 | 13.91 | 5.22 | 9.27 | 7.44 | 3.59 | 13.57 | 4.46 | 15.18 | 5.79 | 15.33 | 6.24 |

TABLE 2a-continued

| Example | EDA | PIP | AEP | DETA | TETA(NC) | TETA(C) | TEPA(NC) | TEPA(C) | HVY(NC) | HVY(C) | AEEA |
|---|---|---|---|---|---|---|---|---|---|---|---|
| 8 | 18.38 | 6.27 | 12.43 | 9.88 | 5.01 | 12.83 | 5.59 | 13.88 | 4.19 | 7.95 | 3.59 | aWeight percent of products is expressed on a feedstock-free, water-free, weight normalized basis.

EXAMPLE 9

A mixture of monoethanolamine (61.5 g, 1.01 moles), ammonia (35.2 g, 2.07 mole), and lanthanum acid phosphate Catalyst B (8.9 g) was reacted according to the procedure of Example 1 under an autogenous pressure of 1,500 psig. Analysis of the cooled reaction mixture by gas-liquid chromatography indicated substantial conversion of monoethanolamine to a mixture of polyamines. Tables 3 and 4 set forth additional details.

EXAMPLES 10-16

The procedure of Example 9 was repeated with representative Group IIIB metal acid phosphate-B catalysts. Catalysts designated as "metal and phosphate-B" were prepared from the corresponding metal nitrate and ammonium dihydrogen phosphate by the procedure exemplified for lanthanum acid phosphate Catalyst B. Additional experimental details and product analysis are shown in Tables 3 and 4.

relatively low reaction temperature (Examples 9 and 15), or a relatively short reaction time (Example 4), aminoethylethanolamine (AEEA) is formed in moderate to good yield. This coproduct of polyamine formation is a commercially valuable intermediate for production of, for example, non-ionic surfactants and urethane catalysts.

Use of increasing catalyst levels at a fixed reaction time and temperature provides higher conversions of monoethanolamine to polyamines (Examples 5 and 6, 10-12). Selectivity to noncyclic polyamines as a proportion of the total product mixture may also increase as conversion increases owing to conversion of aminoethylethanolamine to both noncyclic polyamines by alkylation of ammonia and cyclic polyamines by intramolecular alkylation. However, as very high conversions of monoethanolamine are attained, selectivity to noncyclic polyamines may decrease from an optimum level (Examples 10-12). At high conversions of monoethanolamine, water-mediated reforming of polyamines

TABLE 3

| Example | Catalyst | Catalyst Level (Wt. %)a | Temp (°C.) | Time (hr) | Mole Ratio (MEA/NH$_3$)b | Conversionc (%)d | Selectivity (NC)e | Selectivity (AEEA)f |
|---|---|---|---|---|---|---|---|---|
| 9 | Lanthanum Acid Phosphate-B | 14.5 | 280 | 2 | 1/2 | 68 | 29 | 23 |
| 10 | Lanthanum Acid Phosphate-B | 3.6 | 300 | 2 | 1/2 | 58 | 27 | 23 |
| 11 | Lanthanum Acid Phosphate-B | 7.4 | 300 | 2 | 1/2 | 72 | 41 | 10 |
| 12 | Lanthanum Acid Phosphate-B | 14.5 | 300 | 2 | 1/2 | 79 | 31 | 10 |
| 13 | Praseodymium Acid Phosphate-B | 7.2 | 300 | 2 | 1/2 | 50 | 20 | 24 |
| 14 | Dysprosium Acid Phosphate-B | 7.3 | 300 | 2 | 1/2 | 63 | 27 | 17 |
| 15 | Samarium Acid Phospahte-B | 7.4 | 280 | 2 | 1/2 | 49 | 27 | 48 |
| 16 | Samarium Acid Phosphate-B | 7.3 | 300 | 2 | 1/2 | 69 | 20 | 15 | aBased on monoethanolamine (MEA).
bMole ratio of monoethanolamine:ammonia in the feedstock.
cResults are derived from analyses presented in Table 4, and are rounded off to the nearest integer.
dBased on unchanged monoethanolamine.
eWeight percent of linear and branched polyethylene amines in total polyamine product.
fWeight percent of aminoethylethanolamine (AEEA) in total polyamine product.

TABLE 4a

| Example | EDA | PIP | AEP | DETA | TETA(NC) | TETA(C) | TEPA(NC) | TEPA(C) | HVY(NC) | NVY(C) | AEEA |
|---|---|---|---|---|---|---|---|---|---|---|---|
| 9 | 9.56 | 4.96 | 9.66 | 7.99 | 3.67 | 14.19 | 5.10 | 13.09 | 2.43 | 6.31 | 23.04 |
| 10 | 12.89 | 6.64 | 11.00 | 5.59 | 3.56 | 14.59 | 3.88 | 13.18 | 1.38 | 4.54 | 22.76 |
| 11 | 19.07 | 5.35 | 9.26 | 8.62 | 4.48 | 14.95 | 5.35 | 12.07 | 3.96 | 6.38 | 10.50 |
| 12 | 12.34 | 4.50 | 11.27 | 7.80 | 4.49 | 11.79 | 5.37 | 14.14 | 1.35 | 16.57 | 10.37 |
| 13 | 8.76 | 6.10 | 10.38 | 2.74 | 2.42 | 14.51 | 2.57 | 13.74 | 3.33 | 11.71 | 23.74 |
| 14 | 14.29 | 7.72 | 12.00 | 4.75 | 3.44 | 15.67 | 3.27 | 14.32 | 1.21 | 5.93 | 17.39 |
| 15 | 17.42 | 6.05 | 6.44 | 4.93 | 2.30 | 8.35 | 2.51 | 3.88 | 0.00 | 0.00 | 48.42 |
| 16 | 8.47 | 7.18 | 12.70 | 3.17 | 2.55 | 17.96 | 2.48 | 17.56 | 2.48 | 9.89 | 14.75 | aWeight percent of products is expressed on a feedstock-free, water-free, weight-normalized bases.

From the data shown in Tables 1-4 for examples 1-16 it can be readily seen that the reactions of monoethanolamine with ammonia catalyzed by Group IIIB metal acid phosphates form a wide range of polyamine products with generally high conversions of monoethanolamine. Selectivity to noncyclic polyamines is usually low, that is to say less than about 50 wt %. With relatively low levels of catalyst (Examples 5, 10, 13, 14 and 16), a relatively high level of ammonia (Example 2), may generate cyclic polyamines (See U.S. Pat. Nos. 4,316,840 and 4,316,841).

As reaction time is increased at a fixed reaction temperature and catalyst level, higher conversions of monoethanolamine are obtained (Examples 4 and 6). Again, selectivity to noncyclic polyamines as a proportion of the total product mixture may also increase owing to conversion of aminoethylethanolamine to both noncyclic and cyclic polyamines.

With an increased level of ammonia at a fixed reaction temperature and catalyst level, selectivity to noncyclic polyamines may increase markedly (Examples 1 and 2). Inclusion of an increased amount of ammonia not only dilutes the reaction which necessitates use of longer reaction times to attain high conversions of monoethanolamine, but also favors amination of aminoethylethanolamine to form noncyclic polyamines at the expense of intramolecular cyclization to form cyclic polyamines.

As reaction temperature is increased at a fixed catalyst level and reaction time, higher conversions of monoethanolamine are obtained (Examples 9 and 12, 15 and 16). However, despite transformation of the intermediate aminoethylethanolamine to polyamines, selectivity to noncyclic polyamines either changes little (Examples 9 and 12) or decreases (Examples 15 and 16). Consequently, intramolecular alkylation of aminoethylethanolamine to form a greater proportion of cyclic polyamines is favored by higher reaction temperatures, while amination of aminoethylethanolamine to form a greater proportion of noncyclic polyamines is favored by increased concentrations of ammonia in the reaction, or, up to a maximum concentration of noncyclic polyamines, by increased reaction times or catalyst levels.

EXAMPLE 17

This example was carried out in a fixed bed packed reactor, and demonstrated continuous production of polyamines from monoethanolamine and dimethylamine with a supported Group IIIB metal acid phosphate.

Lanthanum acid phosphate-B supported (16 wt. % catalyst incorporation) on a low surface area macroporous inert alumina carrier (5 cm³ of −12 to −18 mesh particles) was charged to a fixed bed reactor (26 cm³ total volume) and overlaid with crushed vicor (5 cm³ of −12 to −18 mesh particles). The reactor was heated to 255° C. A mixture of monoethanolamine (MEA) and dimethylamine (DMA) (mole ratio MEA:DMA was 1:6) was passed over the catalyst at a liquid hourly space velocity of 10.0 hr⁻¹, based on total feed, at a pressure of 300 psig. Analysis of the cooled reaction mixture indicated substantial conversion of monoethanolamine to a mixture of polyamines. See Tables 5 and 6 for additional data.

TABLE 5

| Example | Catalyst | LHSV (hr⁻¹)[a] | Temp (°C.) | Press (psig) | Mole Ratio (MEA/DMA) | Conversion (%)[b] | Selectivity (NC)[c] | (AEEA)[d] |
|---|---|---|---|---|---|---|---|---|
| 17 | Lanthanum Acid Phosphate-B | 10.0 | 225 | 300 | 1:6 | 42 | 37 | 7 |

[a]Based on monoethanolamine and dimethylamine.
[b]Based on monoethanolamine
[c]Weight percent of linear and branched polyethylene amines in total polyamine product
[d]Weight percent of amoinoethylethanolamine (AEEA) in total polyamine product.

TABLE 6[a]

| Example | DMEDA[b] | PIP[c] | AEP[d] | DMDETA[e] | DMTETA(NC)[f] | TETA(C)[g] | DMTEPA(NC)[h] | TEPA(C)[i] | AEEA[j] |
|---|---|---|---|---|---|---|---|---|---|
| 17 | 19.23 | 8.51 | 14.58 | 15.36 | 1.49 | 22.80 | 0.89 | 10.00 | 7.14 |

[a]Weight percent of products is expressed on a feedstock-free, water-free, weight-normalized basis
[b]N,N—dimethylethylenediamine
[c]Piperazine
[d]Aminoethylpiperazine
[e]N,N—dimethyldiethylenetriamine
[f]N,N—dimethyltriethylenetetramine (noncyclic product)
[g]Triethylenetetramine (cyclic isomers)
[h]N,N—dimethyltetraethylenepentamine (noncyclic product)
[i]Tetraethylenepentamine (cyclic isomers)
[j]Aminoethylethanolamine

COMPARATIVE EXAMPLES 18-25

The following comparative examples 18-22 and 24-25 illustrate that alkali metal (Group IA) and alkaline earth (Group IIA) acid phosphates were less effective catalysts, even at high levels of incorporation, for the production of polyethylene polyamines from monoethanolamine and ammonia. The procedure of the previous examples was followed with the experimental details set forth in Tables 7 and 8.

For comparative Example 23, a mixture of monoethanolamine (61.0 g, 1.00 mole), ammonia (40.1 g, 2.36 mole), and Duolite ES-467 (15.6 g of the sodium form; approximately 0.01 mole of methylenephosphonate groups are present) was placed in a 300 wt. stainless steel stirred autoclave. Duolite ES-467 resin is marketed by Diamond Shamrock Corp. The mole ratio of ammonia:monoethanolamine was 2.36:1.00; catalyst incorporation was 1.00 mole % based on monoethanolamine. The mixture was heated to 300° C. for 2.0 hours, during which time autogeneous pressure of 2900 psig developed. During the reaction, the mixture was stirred at 2000 rpm. Analysis of the cooled reactor mixture indicated that small amounts of polyethylene amines had been formed. See Tables 7 and 8.

TABLE 7

| Comparative Example | Catalyst | Catalyst Level (wt %)[a] | Temp (°C.) | Time (hr) | Mole Ratio (MEA/NH₃)[b] | Conversion[c] (%)[d] | Selectivity[c] (NC)[e] | (AEEA)[f] |
|---|---|---|---|---|---|---|---|---|
| 18 | Strontium Monohydrogen Phosphate | 30.1 | 300 | 2 | 1/4 | 9 | 40 | 56 |
| 19 | Barium Monohydrogen Phosphate | 32.8 | 300 | 2 | 1/2 | 19 | 24 | 76 |
| 20 | Sodium | 4.6 | 300 | 2 | 1/2 | 20 | 29 | 66 |

TABLE 7-continued

| Comparative Example | Catalyst | Catalyst Level (wt %)[a] | Temp (°C.) | Time (hr) | Mole Ratio (MEA/NH$_3$)[b] | Conversion[c] (%)[d] | Selectivity[c] (NC)[e] | (AEEA)[f] |
|---|---|---|---|---|---|---|---|---|
| | Monohydrogen Phosphate | | | | | | | |
| 21 | Potassium Monohydrogen Phosphate | 5.7 | 300 | 2 | 1/2 | 13 | 2 | 80 |
| 22 | Strontium Monohydrogen Phosphate | 5.9 | 300 | 2 | 1/2 | 5 | 29 | 58 |
| 23 | Duolite ES-467 Resin, Sodium Form | 25.6 | 300 | 2 | 1/2.4 | 27 | 33 | 45 |
| 24 | Strontium Dihydrogen Phosphate | 9.0 | 300 | 2 | 1/2 | 24 | 4 | 65 |
| 25 | Potassium Dihydrogen Phosphate | 4.3 | 300 | 2 | 1/2 | 23 | 28 | 56 |

[a]Based on monoethanolamine (MEA).
[b]Mole ratio of monoethanolamine:ammonia in the feedstock.
[c]Results are derived from analyses presented in Table 6, and are rounded off to the nearest integer.
[d]Based on unchanged monoethanolamine.
[e]Weight percent of linear and branched polyethylene amines in total polyamine product.
[f]Weight percent of aminoethylethanolamine (AEEA) in total polyamine product.

TABLE 8

| Comparative sample | EDA | PIP | AEP | DETA | TETA(NC) | TETA(C) | TEPA(NC) | TEPA(C) | HVY(NC) | HVY(C) | AEEA |
|---|---|---|---|---|---|---|---|---|---|---|---|
| 18 | 37.28 | 2.27 | 1.67 | 1.67 | 0.00 | 0.00 | 0.00 | 0.00 | 0.00 | 0.00 | 56.10 |
| 19 | 16.14 | 0.49 | 0.00 | 7.58 | 0.00 | 0.00 | 0.00 | 0.00 | 0.00 | 0.00 | 75.78 |
| 20 | 26.45 | 2.98 | 1.82 | 2.64 | 0.00 | 0.00 | 0.00 | 0.00 | 0.00 | 0.00 | 66.12 |
| 21 | 2.37 | 4.42 | 12.01 | 0.00 | 0.00 | 1.26 | 0.00 | 0.00 | 0.00 | 0.00 | 79.94 |
| 22 | 29.49 | 4.24 | 8.69 | 0.00 | 0.00 | 0.00 | 0.00 | 0.00 | 0.00 | 0.00 | 57.58 |
| 23 | 26.03 | 9.61 | 3.92 | 4.32 | 2.68 | 6.67 | 0.00 | 1.90 | 0.00 | 0.00 | 44.87 |
| 24 | 20.98 | 4.79 | 5.57 | 2.07 | 0.65 | 0.52 | 0.00 | 0.00 | 0.00 | 0.00 | 65.41 |
| 25 | 19.70 | 6.54 | 4.42 | 5.93 | 1.98 | 5.63 | 0.00 | 0.00 | 0.00 | 0.00 | 55.8 |

[a]Weight percent of products is expressed on a feedstock-free, water-free, weight-normalized basis.

The prior art requires a source of preformed ethylenediamine for reaction with monoethanolamine to produce polyethylene amines. The production of ethylenediamine is an additional process step which extends and complicates the prior art routes to polyethylene amines. Thus, production of polyethylene amines requires preparation of monoethanolamine, the alkylating agent, and ethylenediamine, the aminating agent, in separate steps and subsequent copolymerization of the monomers to provide polyethylene amines.

In contrast, the process of this invention involves reaction of monoethanolamine with ammonia which is a fundamental feedstock and a simple aminating agent. Polyethylene amines are obtained directly in good yields from this process. In addition, composition of the product mixture can be controlled by the choice of the appropriate catalyst and process variables such as catalyst level, feed ratio and reaction time. Moreover, the process of this invention does not produce a contaminated inorganic salt co-product that must be separated from amine products and handled separately.

STATEMENT OF INDUSTRIAL APPLICATION

The inventive process for preparing polyalkylene polyamine compounds is applicable to the preparation low molecular weight polyethylene amines which are extensively used in a wide variety of applications. Significant uses of polyethylene amines include their use as corrosion inhibitors, fabric softeners, lubricating oil additives, co-monomers for polyamide resins, fungicides, surfactants, curing agents for epoxy resins and chelating agents.

We claim:

1. A process for preparing a polyalkylene polyamine, which comprises:
   contacting ammonia or a primary or secondary amine with an alkanolamine compound having an amino group and a primary or secondary hydroxy group in the presence of a catalytically effective amount of a Group IIIB metal acid phosphate at a temperature sufficient to effect reaction between the ammonia or amine and the alkanolamine compound under a pressure sufficient to maintain a substantial amount of the ammonia or amine in the reaction zone.

2. The process of claim 1 in which the Group IIIB metal is scandium, yttrium, lanthanum or a rare earth lanthanide having an atomic number from 58 to 71.

3. The process of claim 2 wherein the catalyst is a Group IIIB dihydrogen phosphate.

4. The process of claim 2 wherein the catalyst is a Group IIIB monohydrogen phosphate.

5. The process of claim 3 in which the catalyst is the dihydrogen phosphate salt of lanthanum, praseodymium, dysprosium or samarium.

6. The process of claim 4 wherein the catalyst is a monohydrogen phosphate salt of lanthanum, neodymium, yttrium, gadolinium or praseodymium.

7. The process of claim 1 wherein the temperature is from about 175° C. to 400° C.

8. The process of claim 1 wherein the molar ratio of the ammonia or amine to the alkanolamine is from 1:1 to 10:1.

9. The process of claim 1 wherein the amount of Group IIIB metal acid phosphate is from 0.1 to 25 weight % based upon alkanolamine.

10. A process for preparing polyalkylene polyamines which comprises:

(a) contacting ammonia and an alkanolamine compound having a primary or secondary hydroxyl group of the general formula:

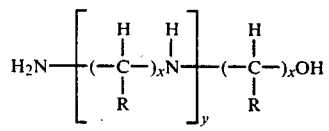

wherein R is hydrogen or a lower alkyl ($C_1$-$C_4$) radical, x is a number from 2 to about 6, and y is a number from 0 to about 3, in the presence of a catalytically effective amount of an acid phosphate salt of a Group IIIB metal at a temperature from about 210° C. to about 350° C. under a pressure sufficient to maintain a substantial amount of the ammonia in the reaction zone, and (b) recovering the polyalkylene polyamine from the resultant reaction mixture.

11. The process of claim 10 in which the catalyst is an acid phosphate salt of a Group IIIB metal which is scandium, yttrium, lanthanum or a rare earth lanthanide having an atomic number from 58 to 71.

12. The process of claim 11 in which the alkanolamine is an ethanolamine when R is hydrogen or a lower alkyl ($C_1$-$C_4$) radical, x is 2 and y is 0 to 3.

13. The process of claim 12 in which the alkanolamine is monoethanolamine.

14. The process of claim 13 in which the catalyst is a Group IIIB monohydrogen phosphate.

15. The process of claim 13 in which the catalyst is a Group IIIB dihydrogen phosphate.

16. The process of claim 14 in which the catalyst is a monohydrogen phosphate salt of lanthanum, neodymium, yttrium, gadolinium or praseodymium.

17. The process of claim 15 in which the catalyst is a dihydrogen phosphate salt of lanthanum, praseodymium, dysprosium or samarium.

18. The process of claim 13 in which the metal is lanthanum.

19. The process of claim 13 in which the metal is neodymium.

20. A process for preparing polyalkylene polyamines, which comprises:

contacting ammonia or an amine of the general formula:

where R' is independently hydrogen or an alkyl ($C_1$-$C_{24}$) radical, with an alkanolamine compound having an amino group and a primary or secondary hydroxy group of the general formula:

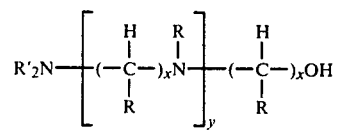

where R is hydrogen or a lower alkyl ($C_1$-$C_4$) radical, R' is hydrogen or an alkyl ($C_1$-$C_{24}$) radical, x is a number from 2 to 6, y is a number from 0 to 3, in the presence of a catalytically effective amount of a Group IIIB metal acid phosphate at a temperature from about 175° C. to about 400° C. under a pressure sufficient to maintain a substantial amount of the ammonia or amine in the reaction zone.

21. The process of claim 20 in which the Group IIIB metal is scandium, yttrium, lanthanum or the rare earth lanthanide having an atomic number from 58 to 71.

22. The process of claim 21 wherein the catalyst is a Group IIIB dihydrogen phosphate.

23. The process of claim 21 wherein the catalyst is a Group IIIB monohydrogen phosphate.

24. The process of claim 22 in which the catalyst is the dihydrogen phosphate salt of lanthanum, praseodymium, dysprosium or samarium.

25. The process of claim 23 wherein the catalyst is a monohydrogen phosphate salt of lanthanum, neodymium, yttrium, gadolinium or praseodymium.

26. The process of claim 20 in which the pressure is from 5 to 150 atmospheres.

27. The process of claim 20 wherein the molar ratio of the ammonia or amine to the alkanolamine is from 1:1 to 10:1.

28. The process of claim 20 wherein the amount of Group IIIB metal acid phosphate is from 0.1 to 25 mole % based upon alkanolamine.

29. The process of claim 20 in which the alkanolamine is contacted with a methylamine.

30. The process of claim 20 in which the alkanolamine is contacted with an ethylamine.

31. A continuous process for preparing a polyalkylene polyamine which comprises (a) adding a charge consisting essentially of ammonia or a primary or secondary amine and an alkanolamine compound having an amino group and a primary or secondary hydroxy group to a reaction zone containing a catalytically effective amount of a Group IIIB metal acid phosphate at a temperature sufficient to effect a reaction between the ammonia or amine, and the alkanolamine compound under a pressure sufficient to maintain a substantial amount of the ammonia or amine in the reaction zone to produce a reaction product stream comprising ammonia or primary or secondary amine, alkanolamine compound, and a polyalkylene polyamine, and (b) withdrawing the product stream from the reaction zone and separating it to provide a polyalkylene polyamine stream and ammonia or the primary or secondary amine and alkanolamine compound which are recycled to the reaction zone.

32. The process of claim 31 in which the charge consists essentially of ammonia and monoethanolamine.

33. The process of claim 32 in which the molar ratio of is maintained from about 5 to 150 atmospheres.

34. The process of claim 31 in which the catalyst is a lanthanum acid phosphate.

35. The process of claim 33 in which the catalyst is a lanthanum acid phosphate.

36. In a continuous process for the preparation of polyalkylene polyamines which comprises continuously adding a feed comprising an alkanolamine compound having a primary amino group and a primary or secondary hydroxy group to a reaction zone containing a catalyst to yield a product stream comprising a polyalkylene polyamine and alkanolamine compound separating the desired polyamine from the product stream and recycling the alkanolamine compound to the reaction zone, the method for avoiding inclusion of alkyleneamine compound in the feed to the reaction zone, which method comprises
  (a) adding ammonia or a primary or secondary alkylamine to the feed to the reaction zone,
  (b) using a catalytically effective amount of a Group IIIB metal acid phosphate as the catalyst, and
  (c) effecting the reaction under a pressure sufficient to maintain a substantial amount of the ammonia or amine in the reaction zone.

37. The method of claim 36 in which unreacted ammonia or amine is recycled to the reaction zone.

38. The method of claim 37 in which the alkanolamine compound is monoethanolamine.

39. The method of claim 38 in which the molar ratio of monoethanolamine:ammonia in the reaction zone is from 1:1 to 1:10.

40. The method of claim 38 in which the catalyst is a lanthanum acid phosphate.

41. The method of claim 40 in which the pressure is from about 5 to 150 atmospheres.

42. The method of claim 41 in which the temperature is from 175° C. to 400° C.

* * * * *

UNITED STATES PATENT AND TRADEMARK OFFICE
CERTIFICATE OF CORRECTION

PATENT NO. : 4578517

DATED : 25 March 1986

INVENTOR(S) : Thomas A. Johnson et al

It is certified that error appears in the above-identified patent and that said Letters Patent is hereby corrected as shown below:

Claim 33, Column 16 should read --The process of claim 32 in which the molar ratio of monoethanolamine:ammonia in the reaction zone is maintained from 1:1 to 1:10 and the pressure is about 5 to 150 atmospheres.--

Signed and Sealed this

Eleventh Day of December, 1990

Attest:

HARRY F. MANBECK, JR.

*Attesting Officer*     *Commissioner of Patents and Trademarks*